US012601683B2

(12) United States Patent
Muller

(10) Patent No.: US 12,601,683 B2
(45) Date of Patent: Apr. 14, 2026

(54) SERIAL MULTICHANNEL MICROSCOPY

(71) Applicant: Miltenyi Biotec B.V. & Co. KG,
Bergisch Gladbach (DE)

(72) Inventor: Werner Muller, Bergisch Gladbach
(DE)

(73) Assignee: Miltenyi Biotec B.V. & Co. KG,
Bergisch Gladbach (DE)

( * ) Notice: Subject to any disclaimer, the term of this
patent is extended or adjusted under 35
U.S.C. 154(b) by 988 days.

(21) Appl. No.: 17/768,276

(22) PCT Filed: Nov. 11, 2020

(86) PCT No.: PCT/EP2020/081731
§ 371 (c)(1),
(2) Date: Apr. 12, 2022

(87) PCT Pub. No.: WO2021/094356
PCT Pub. Date: May 20, 2021

(65) Prior Publication Data
US 2024/0133810 A1    Apr. 25, 2024
US 2024/0230534 A9    Jul. 11, 2024

(30) Foreign Application Priority Data

Nov. 11, 2019    (EP) .................................... 19208229

(51) Int. Cl.
*G01N 21/64*        (2006.01)
*G01N 33/58*        (2006.01)
(52) U.S. Cl.
CPC ..... *G01N 21/6428* (2013.01); *G01N 21/6458*
(2013.01); *G01N 33/582* (2013.01); *G01N*
*2021/6439* (2013.01)

(58) Field of Classification Search
CPC ........... G01N 21/6428; G01N 21/6458; G01N
33/58; G01N 33/582; G01N 2021/6439
See application file for complete search history.

(56) References Cited

PUBLICATIONS

"Release Technology:Controlled release of anitbody-Fluorochorome conjugates," Pankratz et al. Cancer Research, vol. 79, No. 13, Suppl. May 1, 2010 p. 4048.
"Expresion of drebin E in migrating neuroblast in adult rat Brain," Song et al, Neuroscience vol. 152, No. 3, Jan. 19, 2008 p. 760-687.
"MACSima (TM) Imaging platformprovides new insights into cancer biology," C. Herbel et al., MACS & more, ol 18, No. 1, Aug. 2, 2019 p. 16-20.
"Extraction of target fluorescence signal from in vivobackground," L. Fei et al., Intl J of Automation and Computing, vol. 9, No. 3, Jun. 1, 2912.
Photobleaching kinetics of fluorecein in quantitative fluorescence microscopy L. Song, et al.,BioPhys Journal, vol. 68, No. 6 Jun. 1, 1995 p. 2588-2600.

*Primary Examiner* — Kathryn Elizabeth Limbaugh
(74) *Attorney, Agent, or Firm* — Jacquelin K Spong

(57) ABSTRACT

The invention is directed to a much faster way of combining multiple colour channels in fluorescence microscopy for complex fast diagnostic and research purposes. The advantage is that the procedure and the microscope setting can be simplified and miniaturised to an extend that the construction of such automatic systems become much easier and by omitting the erasing step the speed of analysis is faster and moved to the processing of the images by image processing systems, nowadays working at almost real time.

11 Claims, 3 Drawing Sheets a        b        c        d        a        b        c        d

Fig. 3

SERIAL MULTICHANNEL MICROSCOPY

BACKGROUND

The present invention is directed to a method for detection of different target moieties on a sample of biological specimens by repetitive fluorescent labelling and imaging of the target moieties without degrading the fluorescent labelling between the imaging steps.

The current approach for repetitive fluorescent labelling and imaging is a cyclic process in which the targets are stained, images are taken, and the staining is removed by oxidation or radiation before a new staining round is started.

For example, EP3037821 discloses a method for detection and separation of a target moiety according to, e.g. a fluorescence signal, with conjugates having an enzymatically-degradable spacer for reversible fluorescent labelling.

PCT/EP2019/060403 discloses conjugates releasable labelling comprising an enzymatically-degradable spacer, wherein the fluorescent quantum yields for detection is increased by inserting a linker unit comprising one or more polyethylene glycol between releasable spacer and fluorescent dye.

Repetitive imaging methods are further known from EP 0810428, EP1181525, EP 1136822 or EP1224472, wherein samples of biological specimen are contacted in sequential cycles with antigen recognizing moieties coupled to a fluorescent moiety, the location of the antigen is detected by the fluorescent moiety and the fluorescent moiety is eliminated. By repeating the steps labelling-detection-elimination protein networks may be mapped, different cell types can be localized and disease-related changes in the proteome can be analyzed.

All these techniques involve a destaining step between the imaging steps. Destaining may involve treatment with chemicals like oxygenation reagents or radiation to destroy the fluorescent label. Besides the undesirable stress for the biological specimen due to this treatment, destaining is a time-consuming process which increases the total process time considerable.

It has been shown that images with multiple informations can be generated by a two step process by adding first one reagent, then take a picture, add the second reagent and take a picture. Such an approach was disclosed for example by JENNIFER PANKRATZ ET AL: "REAlease Technology: Controlled release of antibody-fluorochrome conjugates for maximal flexibility in flow sorting and fluorescence microscopy applications", CANCER RESEARCH, vol. 79, no. 13, Suppl., 1 May 2019 (2019-05-01), page 4048; SONG ET AL: "Expression of drebrin E in migrating neuroblasts in adult rat brain: Coincidence between drebrin E disappearance from cell body and cessation of migration", NEUROSCIENCE, NEW YORK, NY, US, vol. 152, no. 3, 19 Jan. 2008 (2008-01-19), pages 670-682 and CHRISTOPH HERBEL ET AL: "MACSima™ Imaging Platform provides new insights into cancer biology and target discovery by cyclic immunofluorescence-based imaging", MACS & MORE, vol. 18, no. 1, 2 Aug. 2019 (2019-08-02), pages 16-20.

These publications describe methods in which the first reagent recognizes a subset of molecules of one gene product and the second reagent recognizes all molecules of one gene product. In this publication it is then shown how one can differentiate between the various forms by simple image subtractions between the first and the second staining. In the publication the procedure of each step takes several hours due to the procedure chosen.

However, is known that fluorochromes have variable photo stability properties and/or the conjugates used for staining have variable binding constants to the respective targets. Further, some fluorochromes decay faster compared to others when activated by light. Since "activation by light" includes the excitation radiation, the decay of emission over time can not be avoided and a mere subtraction of images might result in wrong or misleading differential images. The decay of fluorescese emission over time is referred to in following as "acquisition bleaching".

SUMMARY

It was therefore an object of the invention to provide a method for detecting different target moieties on a sample of biological specimen by repetitive fluorescent labelling and imaging which does not involve destaining between the imaging steps and which takes optionally into account acquisition bleaching.

It was found that it is possible to subtract the images from different cycles from each other, thereby creating separate images for each target moiety and simultaneously considering acquisition bleaching. Thus, the subtracting process removes the need of destaining.

Accordingly, the invention is directed to a method for detecting target moieties in a sample of biological specimen by the following cycle consisting of:

a) contacting the sample with a first conjugate comprising a first antigen recognizing moiety Y and a first fluorescent moiety X, thereby binding at least a part of the first conjugate to the target moieties recognized by the first antigen recognizing moiety Y b) removing the first conjugates not bond to the target moieties from the sample c) obtaining a first image of the sample thereby detecting the target moieties labelled with the first conjugate repeating steps a) to c) with at least one second conjugate comprising a second antigen recognizing moiety Y' and a second fluorescent moiety X', thereby obtaining at least one second image and wherein the first and second antigen recognizing moiety Y' bind to different target moieties characterized in that the intensity of the first image is reduced by a degradation function and then subtracted from the at least one second image.

FIG. 1 shows a schematic view of a staining of "numbers" with eight different conjugates, wherein acquisition bleaching of 20% per image exposure is included. This means that a specific staining of one round is 20% weaker in the subsequent round and so forth.

The first row shows four rounds of stainings with four different conjugates, 1,2,3,4. After each staining round an image is taken. Then the image of the subsequent round is subtracted from the image of the previous round. The second line shows the resulting image which only shows the specific signal added at the second round.

The third line shows the situation of an overlapping staining from number 1 and number 5. The staining of number 1 is already weaken by the 5 images taken during the 5 cycles and becomes invisible in the subsequent cycles. This partial overlap allows to extract the specific signal in round 5, as shown in the first image of the fourth line of line of the image.

In the method of the invention, serial images are taken in the fluorescence microscope and after each exposure, the intensity of the staining is reduced depending on the stability of the respective fluorochromes used. When fluorescent images are taken, the fluorescence dye degrade over time. The degradation function for each fluorochrome is used to enhance the precision of the subtraction of the images.

The degradation function may be calculated as decrease in intensity according to method disclosed by Song et al in Biophysical Journal, Vol 68 June 1995 p 2588-2600.

In a more simplified approach, the degradation of the fluorescence dye over time is estimated to follow a linear function over time. Since the staining and washing process of the invention is usually performed in a rather time frame of 1 to 10 minutes, the simplified degradation function can be used without loosing too much information. In this variant of the invention, the degradation function is calculated as decrease in intensity of 5-50%, preferable 10-30%.

In both variants, the terms "decrease in intensity" or "acquisition bleaching" refer to a reduction of intensity of the emission of the fluorescence dye between two images. In other words, the reduction of intensity depends on the processing time of the images. The faster the processing time or the sequences of images taken, the smaller the reduction of intensity and the degradation function will be.

For calibration purposes, the reduction of intensity of the emission of the fluorescence dye between two images should be measured depending on the fluorescence dye utilized. That may result in using different degradation functions for different fluorescence dyes.

In this embodiment, for each image in a series of images at each exposure the decay of the fluorochrome can be predicted and subsequently used to perform additional image processing using the specific photo stability property of a pixel in the image based on the previous staining and decay parameters. This allows specially in multiple staining series to space out similar markers in time and to maximise the differential image between two images.

By using antibody combinations that are usually not expressed on the same cell or at the same location, next to each other in the process, the method of the invention provides images in which the staining will build up in the image by adding staining to areas that were not stained in the previous step. By this physical separation of stainings, further improvement of the image subtraction result will be achieved.

By using fluorescence antibodies, the staining intensity of the fluorescence antibody will be reduced every time an image is taken, due to a property called acquisition bleaching. By this the staining intensity of one staining cycle will be weaker after each subsequent cycle.

The serial process of the invention allows miniaturisation of the process and can be performed in a very small chamber on a single view of field. This miniaturisation allows parallelisation of the process with multiple sample analyses.

BRIEF DESCRIPTION OF THE DRAWINGS

FIG. 1 shows the repetitive staining of a specimen by 4 different conjugates;

FIG. 3 shows a simulation of 11 cycles of staining, including the assumption of a 20% acquisition bleaching as the result of taking the image.

DETAILED DESCRIPTION

In serial multichannel microscopy, there are two important factors, the space occupied by antigen recognising moiety reagents and the intensity range of the antigen recognising moiety. The serial multichannel microscopy requires that either the space (area) or the fraction of an intensity range captured by the camera on a given space (area) is measured or defined. The first parameter can be increased by increasing the resolution of the microscope, the second parameter can be influenced by precise spacing of antigen recognising moiety reagent concentrations over the cycles.

Figure 1:
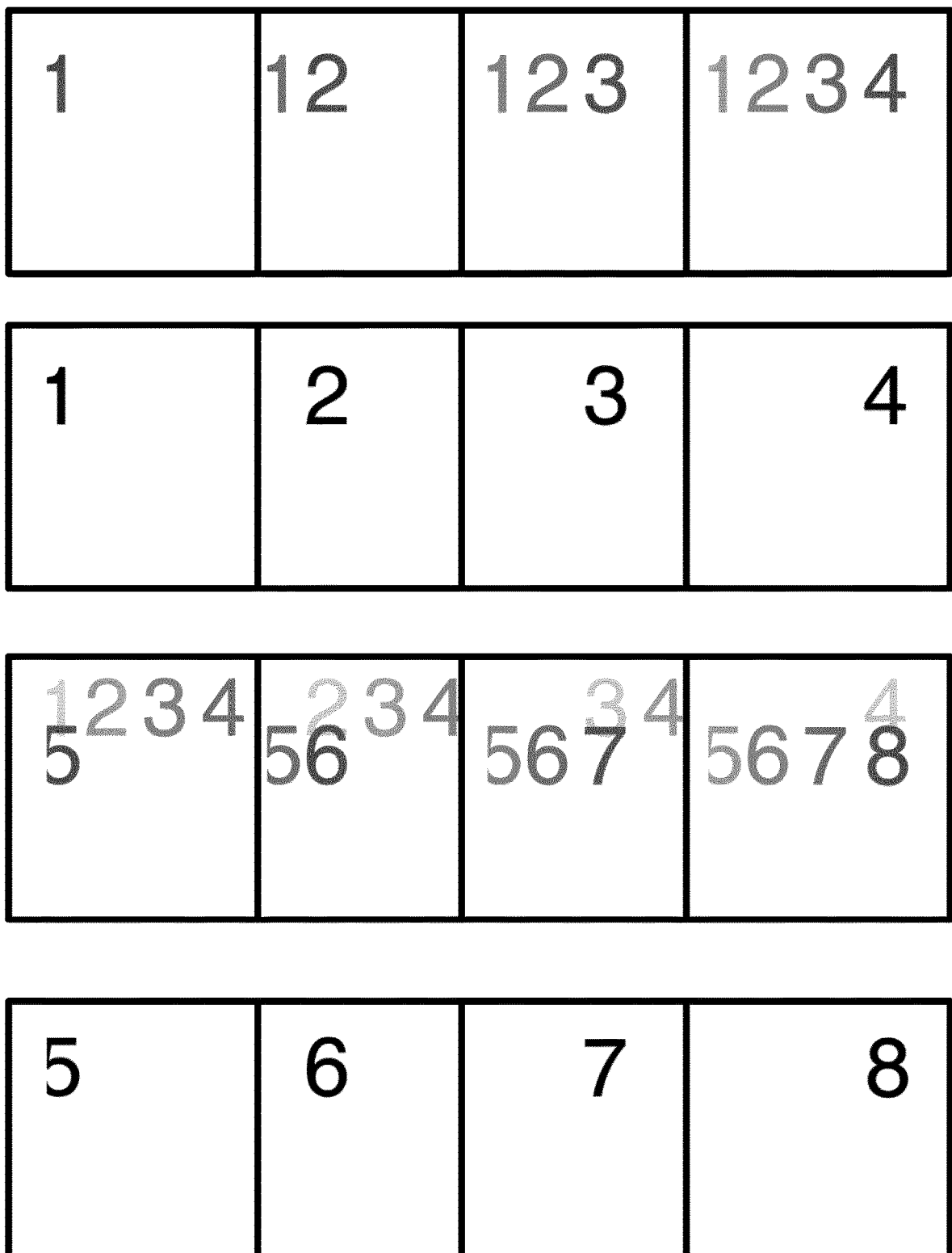
FIG. 1 shows a schematic staining process according to the invention with 8 cycles.

FIG. 1 shows by way of example the method of the invention with a schematic view of a staining of "numbers" with eight different conjugates to demonstate the principle. The first row shows four rounds of stainings with four different conjugates, 1,2,3,4. After each staining round an image is taken. Then the images of the subsequent round is subtracted from the image of the previous round. The second line shows the resulting image which only shows the specific signal added at the second round. In the schematics shown in FIG. 1, a acquisition bleaching of 20% per image exposure is included. This means that a specific staining of one round is 20% weaker in the subsequent round and so forth.

The third line in the schematic view of FIG. shows the situation of an overlapping staining from number 1 and number 5. The staining of number 1 is already weaken by the 5 images taken during the 5 cycles and becomes invisible in the subsequent cycles. This partial overlap allows to extract the specific signal in round 5, as shown in the first image of the fourth line of line of the image. By spacing out overlapping regions in the choice of markers, it is possible to visualise even markers present in the same region of a specimen.

In a first embodiment of the invention, steps a) to c) are repeated in at least 2 cycles, wherein in each cycle an image is obtained and wherein after each cycle the image of the previous cycle is subtracted from the image of the current cycle. In other words, steps a) to c) are repeated in at least 2 cycles, wherein in each cycle an image is obtained and wherein after each cycle a differential image of the current image and the image of the previous cycle is obtained.

In a second embodiment of the invention, steps a) to c) are repeated in at least 2 cycles, wherein in each cycle an image is obtained and wherein after the last cycle, the image of each cycle is subtracted from the image of the respective previous cycle. In other words, steps a) to c) are repeated in at least 2 cycles, wherein in each cycle an image is obtained and wherein after the last cycle, a differential image of each cycle and the respective previous cycle is obtained.

Preferable, steps a) to c) are repeated in 2 to 500 cycles, preferable in 2 to 100 cycles.

In a third embodiment of the invention, the images are obtained as pixel graphic image and the subtraction of the images is obtained by a subtracting algorithm of the pixels.

The conjugates not bond to the target moieties may be removed from the sample by washing.

In the easiest case with the same antigen or same location is recognized multiple times, spacing the use of the second reagents over time in the procedure allows to extent the intensity range, as upon multiple image exposures, the fluorescence intensity of the previous reagent will decay. The function underlying the decay is most likely a multiple exponential function, for example as discussed by Song et al in Biophysical Journal, Vol 68 June 1995 p 2588-2600. Depending on the intensity of the light source and the fluorescence dye, decay can be observed within 1 minute or up to 60 minutes. Only special photoresistant semiconductor-based dyes will not display decay even after several hours (e.g. Quantum dots).

In another embodiment, the fluorescent moieties of the conjugates decay by exposure to radiation. The resulting decay of emission can be calculated as disclosed by Song et al in Biophysical Journal, Vol 68 June 1995 p 2588-2600 and may be used to "space out" the intensities of different staining cycles during the subtraction of the images. Our own measurements reveal realising emission decay of at least 10% per cycle.

By spacing out the use of the second reagent, the difference between the then remaining intensity of the first staining is reduced and the additional fluorescence intensity by the second reagent leads to a bigger difference.

Image Processing

The cyclic multichannel microscopy requires after each staining around to remove the fluorescence staining by various means. This step requires time. The procedure disclosed here allows several channel staining in a serial manner bevor an active removal step for the fluorescence staining is required. By this the acquisition of the multichannel microscopy is accelerated.

When samples are stained with fluorescence detection reagents, areas that are detected by the reagent are labelled and the label is detected in a microscope with the necessary light and detector system.

With the method of the invention, an increase in staining after second staining following a first staining and image acquisition is detected. By simple image processing with the software as already disclosed, the differential picture between the image after the first and the second staining reveals the additional staining by the second fluorescence stain. Depending on the choice of the specificity and intensity of the reagents, multiple serial staining, and image acquisition steps are possible. Also, by choosing small alteration in the colour of the fluorochrome, additional information can be used, if needed, to further improve sensitivity and selectivity between two staining steps.

The method can be used in both a static serial staining and image acquisition step or under continuous flow and continuous imaging under condition where the addition and removal of the staining reagents are controlled by the addition of the reagents to the fluidic system.

Images taken by the fluorescence microscope can processed using known software, for example with the open source software program "FIJI". "FIJI" provides a module "Image Calculator", which may be used to add two images by the function 'Add' and to subtract two images by the function 'Subtract'. The result of the image operation is then shown in a new window and saved in a new image file. Subtracting two images is a feature of many imaging processing programs and such software can be easily obtained.

Similar to the software, the images can be taken by any camera known to a skilled person, for example by Prosilica GT 6600 from Allied Vision.

The staining intensity obtained by staining the sample is dependent on the amount of staining reagent used. One can adjust the amount of the staining reagent used in a way, that the staining is visible to detect the presence or absence of a staining but not by introducing a strong staining reaching the overall capacity of the image detection device. In subsequent staining's, additional staining's can be performed with very well-adjusted staining reagent amount on top of the first staining, resulting in an increase of intensities in case of an overlap staining pattern at positions where both reagents bind. Image calculation procedures can then be used to distinguish single stained pixels vs double stained pixels based on comparison of the staining intensities between images.

The serial multichannel microscopy method of the present invention can be also combined with the known methods in which the staining of fluorescence reagents is removed by known procedures like radiation, oxidative of enzymatic removal of the fluorochrome or the staining reagent. The serial staining procedure also allows the use of other labelling techniques in a serial manner, like labelling of staining reagents by fluorescent oligo probes. Preferable, such other labelling techniques are utilized after the last cycle of the method of the invention.

In another embodiment of the invention, images of the first and second conjugates not bound to the respective target moieties are used to calibrate the decay by exposure to radiation. To this end, the support for the sample may be coated with a protein which is recognized by the conjugates. In a channel not used to stain cells, the fluorochrome decay factor can be determined. With the decay factor, the image subtraction result can be improved.

In another embodiment of the invention, first and second conjugates are used having slightly different absorption spectra or at least absorption maxima at slightly different wavelengths. When using fluorochromes with overlapping absorption spectra, it is possible to use them not at the same time but one after the other. By the different spectrum again it will improve the image subtraction result. Accordingly, the method according to the invention may include that at least two fluorescent moieties Y are provided having absorption maxima differing at least 10 nm.

In another embodiment of the invention, the method is performed as continuous process and images are taken periodically regardless of the staining steps. As result, images of staining and staining decay can be combined to a movie-like sequence. This approach will allow to optimise the timing between the different stains. This "movie" can be a slow-motion movie with a few images taken per minute which is enough to extract the necessary information. The increased time available for taking the images will increase the sensitivity of the images. The increased number of images will improve the result of the differential calculation of specific stainings in a given cycle.

Conjugates Used in the Invention

In general, any conjugate known in the art of fluorescent labelling of cells may be used in the method of the invention. This includes any conjugate provided with a fluorescent moiety X and an antigen recognizing moiety Y. As antigen recognizing moiety Y, any high-affinity (like an antibody) or low-affinity (like a FAB molecule) unit either directly of via a spacer connected to the fluorescent moiety X may be utilized. Conjugates used in the method of the invention may have the general formula (I) $X_o$-$Y_m$, or (II) $(X_o$-L$)_n$-$Y_m$ or (III) $(X_o$-L$)_n$-P-$Y_m$. Further, the conjugates may comprise units allowing the removal of the label from the target cells for example by addition of an enzyme and/or linker units which increase fluorescence quantum yield. Such conjugates may have the general formula (IV) $(X_o$-L$)_n$-P(L)$_f$(X)$_x$-$Y_m$. In the general formulas (I) to (IV), P stands for and enzymatically degradable spacer, L for a covalent bound linker unit L and X for a covalent bound fluorescent moiety X. 1 and x are integer between 0 and 100 and n,o,m are integers between 1 and 100.

Target Moiety

The target moiety to be detected with the method of the invention can be on any biological specimen, like tissues slices, cell aggregates, suspension cells, or adherent cells. The cells may be living or dead. Preferable, target moieties are antigens expressed intracellular or extracellular on biological specimen like whole animals, organs, tissues slices, cell aggregates, or single cells of invertebrates, (e.g., *Caenorhabditis elegans, Drosophila melanogaster*), vertebrates (e.g., *Danio rerio, Xenopus laevis*) and mammalians (e.g., *Mus musculus* and other subspecies, *Rattus* various subspecies, *Homo sapiens*).

Fluorescent Moiety

The terms X and X' refer to different fluorescent moieties and all features disclosed for X are also applicable for X' and vice versa.

Suitable fluorescent moieties are known from the art of immunofluorescence technologies, e.g., flow cytometry or fluorescence microscopy. In these embodiments of the invention, the target moiety labelled with the conjugate is detected by exciting the fluorescent moiety X and detecting the resulting emission (photoluminescence). Useful fluorescent moieties might be small organic molecule dyes, such as xanthene dyes, like fluorescein, or rhodamine dyes, coumarine dyes, cyanine dyes, pyrene dyes, oxazine dyes, pyridyl oxazole dyes, pyrromethene dyes, acridine dyes, oxadiazole dyes, carbopyronine dyes, benzopyrylium dyes, fluorene dyes, or metallo-organic complexes, such as Ru, Eu, Pt complexes. Besides single molecule entities, clusters of small organic molecule dyes, fluorescent oligomers or fluorescent polymers, such as polyfluorene, can also be used as fluorescent moieties. Additionally, fluorescent moieties might be protein-based, such as phycobiliproteins, nanoparticles, such as quantum dots, upconverting nanoparticles, gold nanoparticles, dyed polymer nanoparticles.

The fluorescent moiety X can be covalently coupled to the linker unit L. Methods for covalently conjugation are known by persons skilled in the art. A direct reaction of an activated group either on the fluorescent moiety X or on the linker unit L with a functional group on either the linker unit L or on the fluorescent moiety X or via a heterobifunctional linker molecule, which is firstly reacted with one and secondly reacted with the other binding partner is possible.

For example, fluorescent dyes are available with groups reactive towards amino groups or thiol groups, such as active esters which react with amino groups on the linker unit, for instance N-hydroxysuccinimide esters (NHS), sulfodichlorophenyl esters (SDP), tetrafluorophenyl esters (TFP), and pentafluorophenyl esters (PFP), or Michael acceptors or haloacetyl groups, which react with thiol groups on the linker unit, for instance maleimide groups, iodoacetamide groups, and bromomaleimide groups. A large number of heterobifunctional compounds are available for linking to entities. Illustrative entities include: azidobenzoyl hydrazide, N-[4-(p-azidosalicylamino)butyl]-3'-[2'-pyridyldithio]propionamide), bis-sulfosuccinimidyl suberate, dimethyladipimidate, disuccinimidyltartrate, N-y-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl] aminobenzoate, glutaraldehyde, succinimidyl-[(N-maleimidopropionamido) polyethyleneglycol] esters (NHS-PEG-MAL), and succinimidyl 4-[N-maleimidomethyl] cyclohexane-1-carboxylate. A preferred linking group is 3-(2-pyridyldithio)propionic acid N-hydroxysuccinimide ester (SPDP), or 4-(N-maleimidomethyl)-cyclohexane-1-carboxylic acid N-hydroxysuccinimide ester (SMCC) with a reactive sulfhydryl group on the fluorescent moiety and a reactive amino group on the linker unit.

The conjugate used in the method of the invention may comprise 1 to 100, preferable 2-30 fluorescent moieties X.

Antigen Recognizing Moiety Y

The term "antigen recognizing moiety Y" refers to any kind of molecule which binds against the target moieties expressed intracellular or extracellular on the biological specimens with high enough affinity to remain on the target after washing away the non-bound antigen recognizing moiety. The terms Y and Y' refer to different antigen recognizing moieties and all features disclosed for Y are also applicable for Y' and vice versa.

The term "antigen recognizing moiety Y" relates especially to an antibody, a fragmented antibody, a fragmented antibody derivative, peptide/MHC-complexes targeting TCR molecules, cell adhesion receptor molecules, receptors for costimulatory molecules or artificial engineered binding molecules, peptides, lectins or aptamers, RNA, DNA, oligonucleotides and analogues thereof.

Fragmented antibody derivatives are for example Fab, Fab', F(ab')2, sdAb, scFv, di-scFv, nanobodies. Such fragmented antibody derivatives may be synthesized by recombinant procedures including covalent and non-covalent conjugates containing these kinds of molecules.

The conjugate used in the method of the invention may comprise 1 to 100, preferable 1 to 20 antigen recognizing moieties Y. The interaction of the antigen recognizing moiety with the target moiety can be of high or low affinity. Binding interactions of a single low-affinity antigen recognizing moiety is too low to provide a stable bond with the antigen. Low-affinity antigen recognizing moieties can be multimerized by conjugation to the enzymatically degradable spacer P to furnish high avidity.

Preferable, the term "Antigen recognizing moiety Y" refers to an antibody or Fab directed against antigen expressed by the biological specimens (target cells) intracellular, like FoxP3, CD154, Ki67 or extracellular, like CD3, CD14, CD4, CD8, CD25, CD34, CD56, and CD133.

The antigen recognizing moieties Y, especially antibodies, can be coupled to the spacer P through side chain amino or sulfhydryl groups. In some cases, the glyosidic side chain of the antibody can be oxidized by periodate resulting in aldehyde functional groups.

The antigen recognizing moiety Y can be covalently or non-covalently coupled to the spacer P. Methods for covalent or non-covalent conjugation are known by persons skilled in the art and the same as mentioned for conjugation of the fluorescent moiety X.

Use of the Method

The method of the invention can be used for various applications in research, diagnostics and cell therapy.

In a first use of the invention, biological specimens like cells are detected or isolated for counting purposes i.e. to establish the number of cells from a sample having a certain set of antigens recognized by the antigen recognizing moieties of the conjugate.

In a second use, one or more populations of biological specimens are separated for purification of target cells. Those isolated purified cells can be used in a plurality of downstream applications like molecular diagnostics, cell cultivation, or immunotherapy.

EXAMPLES

Comparative Example

Mouse spleen sections were stained by 4 different mono-clonal antibodies coupled with a fluorochrome. One antibody was used per stain of a section and an image was taken. Then by computer computation, the images were added on top of each other to simulate staining of the section without erasing the staining. In the next step, the individual staining image is revealed by image processing revealing the individual staining image again by subtracting the first single stained image from the second virtual double stained image and so forth.

The antibody used were NK1.1 available from Miltenyi Biotec B.V. & Co. KG as REA 1162 antibody (1), KLRG1, available from available from Miltenyi Biotec B.V. & Co. KG as REA 1016 antibody (2), GR-1 antibody as monoclonal antibody with the clone name RB6-8C5 available from available from Miltenyi Biotec B.V. & Co. KG, CD38 antibody available from available from Miltenyi Biotec B.V. & Co. KG as Rea 616 (4).

FIG. 2 *a* and *b* show the repetitive staining of a specimen by 4 different conjugates without acquisition bleaching, with a) conjugate 1; b) conjugate 1+2; c) conjugate 1+2+3 and d) conjugate 1+2+3+4.

Figures 2A, 2B:
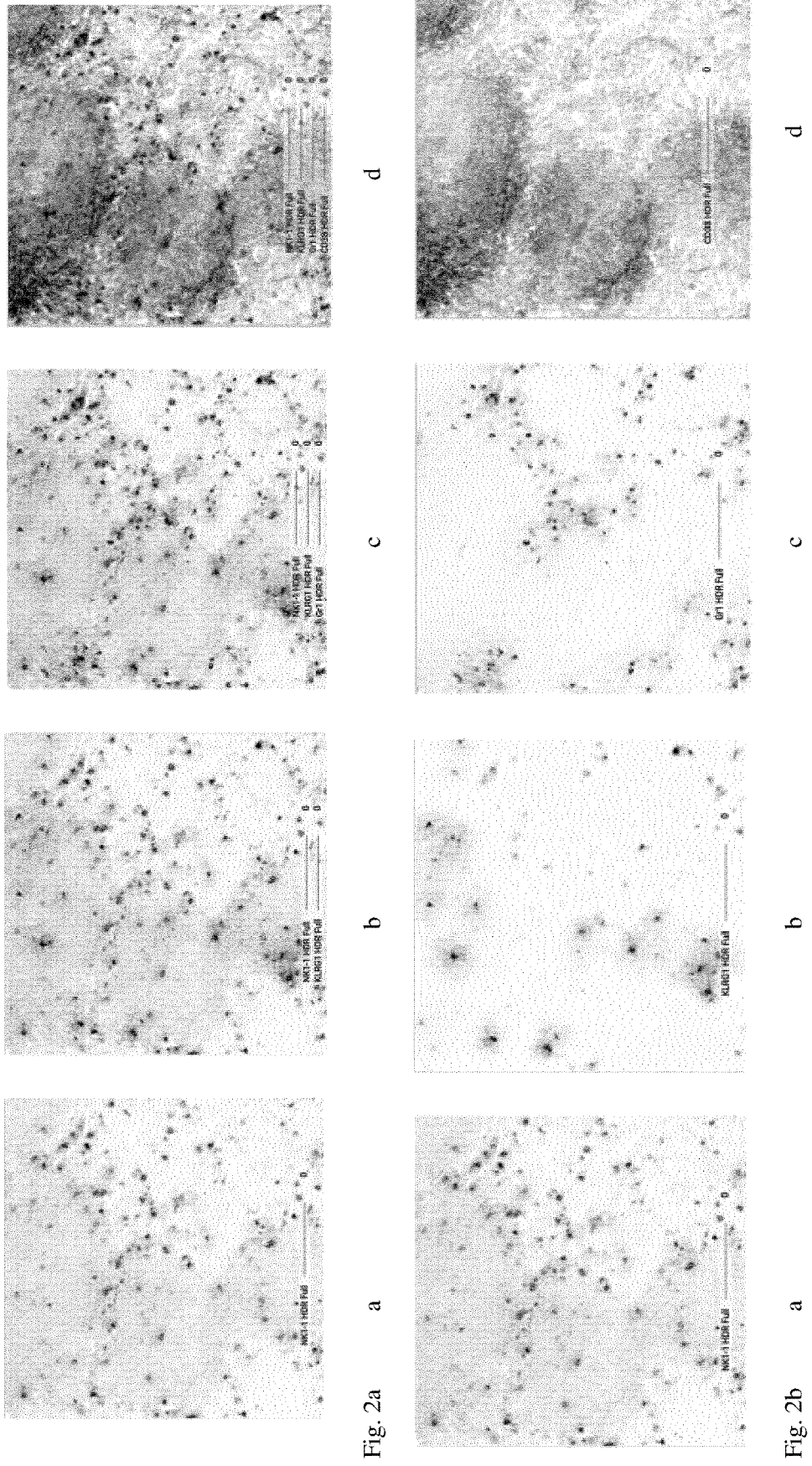
FIG. 2 shows the subtraction of the images of FIG. 1 with a) staining of FIG. 1a); b) staining of FIG. 1b-1a; c) staining of FIG. 1c-(1b+1a) and d) staining of FIG. 1d-(1c+1b+1a).

As result of the method of the invention, FIG. 2*b* shows the subtraction of the images of FIG. 2*a* with a) staining of a); b) staining of image b–a; c) staining of c–(b+a) and d) staining of d–(c+b+a)

Example According to the Invention

In this example, the same tissue section as in FIG. 2 was used but this time the acquisition bleaching as demonstrated in FIG. 1 was included in the simulation of the images. The staining were done using the following 11 antibodies, Ki67 available from Miltenyi Biotec B.V. & Co. KG as REA 183 antibody (A1,A2, cycle 1), KLRG1 available from Miltenyi Biotec B.V. & Co. KG as REA 1016 antibody, (B1,B2, cycle 2), NK1.1 available from Miltenyi Biotec B.V. & Co. KG as REA 1162 antibody, (C1,C2, cycle 3), CD8a available from Miltenyi Biotec B.V. & Co. KG as REA601 antibody (D1, D2, cycle 4), CD1 1b available from Miltenyi Biotec B.V. & Co. KG as REA593, (A3, A4, cycle 5), F4/80 available from Miltenyi Biotec B.V. & Co. KG as REA126, (B3,B4, cycle 6), CD184 available from Miltenyi Biotec B.V. & Co. KG as REA107, (C3,C4, cycle 7), GR-1 antibody as monoclonal antibody with the clone name RB6-8C5 available from Miltenyi Biotec B.V. & Co. KG, (D3, D4, cycle 8), CD15 anti mouse Clone MC-480 antibody from Biolegend, (A5, A6, cycle 9), LY-49A available from Miltenyi Biotec B.V. & Co. KG as REAL436, (B5, B6, cycle 10) and IgM available from Miltenyi Biotec B.V. & Co. KG as REA979 (C5, C6, cycle 11).

After each staining an image is taken and then the next staining is performed and again an image is taken. After each round the staining of the previous rounds are reduced by 20% due to aquistion bleaching (Row A and C). By image subtraction the individual staining can be revealed (Row C and D). Due to the aquistion bleaching effect the number of stainings that can be subsequently performed is greatly enhanced compared to the example shown in FIG. 1. The antibodies used are staining different cell types present in the tissue. By this it is possible to select the antibodies in a way that not the same cell type is stained in directly subsequent rounds.

Figure 3:
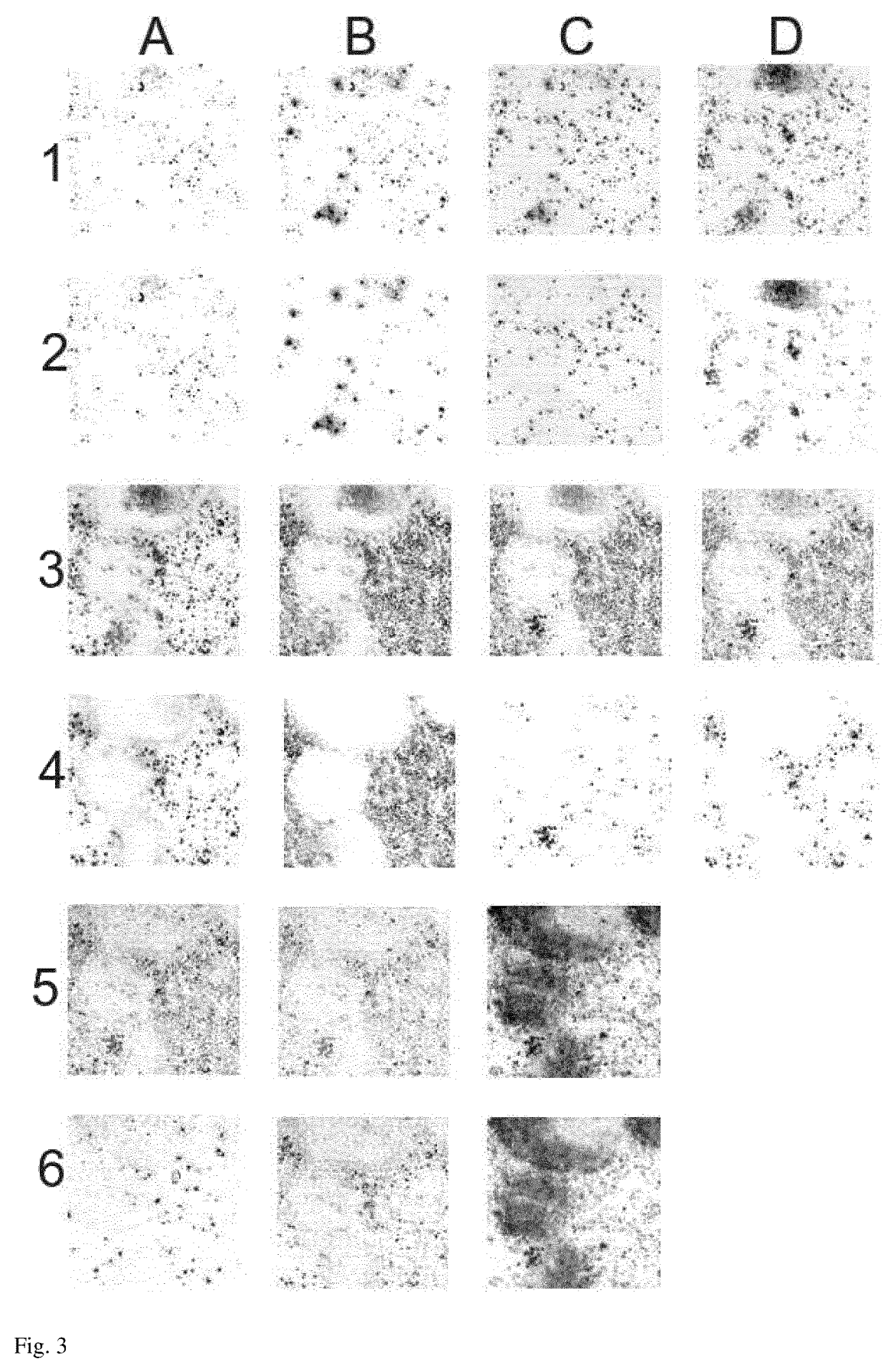

FIG. 3 shows 11 cycles of staining, including the assumption of a 20% acquisition bleaching as the result of taking the image.

The image is organized as a grid. The rows 1, 3, and 5 are the composite images and the rows 2, 4 and 6 show the differential images calculated as described schematically with FIG. 1. The specimen was stained with fluorochrome conjugates. One can see in the images that for example in cycle 4, 1D a strong staining is visible on the top right part of the image. This strong staining is weakened over the subsequent cycles 5, (field 3A), 6, (field 3B), 7, (field 3C) and 8, (field 3D) not visible anymore in cycle 8 shown in field.

The invention claimed is:

1. A method for detecting target moieties in a sample of biological specimen by:
   a) contacting the sample with a first conjugate comprising a first antigen recognizing moiety Y and a first fluorescent moiety X, thereby binding at least a part of the first conjugate to the target moieties recognized by the first antigen recognizing moiety Y
   b) removing the first conjugates not bound to the target moieties from the sample
   c) obtaining a first image of the sample thereby detecting the target moieties labelled with the first conjugate; and
   d) repeating steps a) to c) with at least one second conjugate comprising a second antigen recognizing moiety Y' and a second fluorescent moiety X', thereby obtaining at least one second image and wherein the first and second antigen recognizing moieties Y and Y' bind to different target moieties characterized in that the intensity of the first image is reduced by a degradation function and then subtracted from the at least one second image.

2. The method according to claim 1, characterized in that the degradation function is calculated as a decrease in intensity of 5-50%.

3. The method according to claim 1, characterized in that steps a) to c) are repeated in at least 2 cycles, wherein in each cycle an image is obtained and wherein after each cycle the image of the previous cycle is subtracted from the image of the current cycle.

4. The method according to claim 1, characterized in that steps a) to c) are repeated in at least 2 cycles, wherein in each cycle an image is obtained and wherein after the last cycle, the image of each cycle is subtracted from the image of the respective previous cycle.

5. The method according to claim 1, characterized in that the images are obtained as pixel graphic images and the subtraction of the images is obtained by a subtracting algorithm of the pixels.

6. The method according to claim 1 characterized in that the conjugates not bonded to the target moieties are removed from the sample by washing.

7. The method according to claim 1 characterized in that after the last cycle is performed, the conjugates bonded to the target moieties are removed from the target moieties at least in part by radiation, oxidative or enzymatic treatment.

8. The method according to claim 1 characterized in that the fluorescent moiety X is selected from the group consisting of xanthene dyes, rhodamine dyes, coumarine dyes, cyanine dyes, pyrene dyes, oxazine dyes, pyridyl oxazole dyes, pyromethene dyes, acridine dyes, oxadiazole dyes, carbopyronine dyes, benzpyrylium dyes, fluorene dyes, fluorescent oligomers or fluorescent polymers.

9. The method according to claim 1, characterized in that the fluorescent moieties of the conjugates decay by exposure to radiation.

10. The method according to claim 1, characterized in that images of the first and second conjugates not bound to the respective target moieties are used to calibrate the decay by exposure to radiation.

11. The method according to claim 1, characterized in that the two fluorescent moieties X and X' provided have absorption maxima differing by at least 10 nm.

\* \* \* \* \*